US011471517B2

(12) United States Patent
Serody et al.

(10) Patent No.: US 11,471,517 B2
(45) Date of Patent: Oct. 18, 2022

(54) COMPOSITIONS AND METHODS FOR PREVENTING AND TREATING GRAFT VERSUS HOST DISEASE

(71) Applicants: The University of North Carolina at Chapel Hill, Chapel Hill, NC (US); Regents of the University of Minnesota, Minneapolis, MN (US)

(72) Inventors: Jonathan Serody, Chapel Hill, NC (US); James Coghill, Chapel Hill, NC (US); Danny Bruce, Chapel Hill, NC (US); Bruce Blazar, Golden Valley, MN (US); Heather Stefanski, Minneapolis, MN (US); Benjamin Vincent, Chapel Hill, NC (US)

(73) Assignees: The University of North Carolina at Chapel Hill, Chapel Hill, NC (US); Regents of the University of Minnesota, Minneapolis, MN (US)

( * ) Notice: Subject to any disclaimer, the term of this patent is extended or adjusted under 35 U.S.C. 154(b) by 181 days.

(21) Appl. No.: 16/598,914

(22) Filed: Oct. 10, 2019

(65) Prior Publication Data
US 2020/0155656 A1    May 21, 2020

Related U.S. Application Data

(62) Division of application No. 15/532,740, filed as application No. PCT/US2015/064001 on Dec. 4, 2015, now abandoned.

(60) Provisional application No. 62/087,340, filed on Dec. 4, 2014.

(51) Int. Cl.
*A61K 39/00* (2006.01)
*A61K 35/17* (2015.01)
*A61K 35/12* (2015.01)
*A61K 35/28* (2015.01)
*C12N 5/078* (2010.01)
*A61P 11/00* (2006.01)

(52) U.S. Cl.
CPC ............ *A61K 39/001* (2013.01); *A61K 35/17* (2013.01); *A61K 35/28* (2013.01); *A61P 11/00* (2018.01); *C12N 5/0634* (2013.01); *C12N 5/0651* (2013.01); *A61K 2035/122* (2013.01); *A61K 2035/124* (2013.01); *A61K 2039/5154* (2013.01); *A61K 2039/577* (2013.01); *C12N 2501/2307* (2013.01); *C12N 2501/2333* (2013.01)

(58) Field of Classification Search
CPC .. A61K 35/17; A61K 35/28; A61K 2035/122; A61K 2035/124; A61P 11/00; C12N 5/0634; C12N 2501/2333
See application file for complete search history.

(56) References Cited

U.S. PATENT DOCUMENTS

| | | | |
|---|---|---|---|
| 2009/0148419 A1* | 6/2009 | Gonzalez De La Pena | A61P 37/06 424/93.7 |
| 2009/0208517 A1 | 8/2009 | Moser et al. | |
| 2012/0207727 A1 | 8/2012 | Blazar et al. | |
| 2016/0223749 A1 | 8/2016 | Coolbaugh et al. | |
| 2016/0304574 A1* | 10/2016 | Sharma | C07K 14/54 |
| 2017/0360907 A1 | 12/2017 | Serody et al. | |

FOREIGN PATENT DOCUMENTS

| WO | WO 2014/072446 A1 | 5/2014 |
|---|---|---|
| WO | WO 2016/090250 A1 | 6/2016 |

OTHER PUBLICATIONS

Shankar et al. Idiopathic pneumonia syndrome after bone marrow transplantation: the role of pre-transplant radiation conditioning and local cytokine dysregulation in promoting lung inflammation and fibrosis. International Journal of Experimental Pathology, 82, 101-113 (Year: 2001).*
Wenger et al. Incidence, Risk Factors, and Outcomes of Idiopathic Pneumonia Syndrome after Allogeneic Hematopoietic Cell Transplantation. Biol Blood Marrow Transplant 26 (2020) 413-420 (Year: 2020).*
Shlomchik. Graft-versus-host disease. Nature Reviews, vol. 7, p. 340-352. (Year: 2007).*
Carlson et al. (2009) In vitro-differentiated TH17 cells mediate lethal acute graft-versus-host disease with severe cutaneous and pulmonary pathologic manifestations. Blood 113(6):1365-1374.
Coghill et al. (2010) Separation of graft-versus-host disease from graft-versus-leukemia responses by targeting CC-chemokine receptor 7 on donor T cells. Blood 115(23):4914-22.
Cupedo (2014) Innate protection from graft-versus-host disease. Blood 124(5):673-675.
Fulton et al. (2012) Attenuation of acute graft-versus-host disease in the absence of the transcription factor RORgammat. Journal of immunology 189(4):1765-72.
Hanash et al. (2012) Interleukin-22 protects intestinal stem cells from immune-mediated tissue damage and regulates sensitivity to graft versus host disease. Immunity 37(2):339-50.
Hazenberg et al. (2014) Human innate lymphoid cells. Blood 124(5):700-709.
Kiessling et al. (1976) Killer cells: a functional comparison between natural, immune T-cell and antibody-dependent in vitro systems. J Exp Med. 143(4):772-780.
Lefrancais et al. (2014) Central domain of IL-33 is cleaved by mast cell proteases for potent activation of group-2 innate lymphoid cells. Proceedings of the National Academy of Sciences. 111(43):15502-15507.

(Continued)

*Primary Examiner* — Taeyoon Kim
(74) *Attorney, Agent, or Firm* — Jenkins, Wilson, Taylor & Hunt, P.A.

(57) ABSTRACT

ILC2 cells play a role in the pathogenesis of graft versus host disease (GvHD) and idiopathic pneumonia syndrome (IPS), both conditions associated with allogeneic stem cell transplantation. Infusion of IL-33 activated ILC2 cells into patients with ongoing GvHD or IPS, or prior to onset of GvHD or IPS in susceptible patients, substantially ameliorates the disease and improves survival.

8 Claims, 12 Drawing Sheets

(56) References Cited

OTHER PUBLICATIONS

Mjosberg et al. (2011) Human IL-25- and IL-33-responsive type 2 innate lymphoid cells are defined by expression of CRTH2 and CD161. Nat Immunol 12(11):1055-1062.

Munneke et al. (2014) Activated innate lymphoid cells are associated with a reduced susceptibility to graft-versus-host disease. Blood 124(5):812-821.

Neill et al. (2010) Nuocytes represent a new innate effector leukocyte that mediates type-2 immunity. Nature. 464(7293):1367-70.

Notification of Transmittal of the International Search Report for PCT Application No. PCT/US2015/064001 dated Feb. 16, 2016.

Office Action (Restriction Requirement) corresponding to U.S. Appl. No. 15/532,740 dated Aug. 13, 2018.

Office Action corresponding to U.S. Appl. No. 15/532,740 dated Apr. 11, 2019.

Office Action corresponding to U.S. Appl. No. 15/532,740 dated Nov. 6, 2018.

Panoskaltsis-Mortari et al. (2004) In vivo imaging of graft-versus-host-disease in mice. Blood 103(9):3590-8.

Van Den Brink et al. (2000) Fas-deficient lpr mice are more susceptible to graft-versus-host disease. Journal of immunology 164(1):469-80.

Yi et al. (2009) Reciprocal differentiation and tissue-specific pathogenesis of Th1, Th2, and Th17 cells in graft-versus-host disease. Blood 114(14):3101-3112.

Yu et al. (2014) TNF superfamily member TL1A elicits type 2 innate lymphoid cells at mucosal barriers. Mucosal Immunology 7(3):730-740.

Bartemes et al. IL-33-Responsive Lineage-CD25+CD44hi Lymphoid Cells Mediate Innate Type-2 Immunity and Allergic Inflammation in the Lungs. J Immunol. Feb. 1, 2012; 188(3): 1503-1513. (Year: 2012).

Drake et al. Group 2 Innate Lymphoid Cells and CD4+ T Cells Cooperate to Mediate Type 2 Immune Response in Mice. Allergy. Oct. 2014; 69(10): 1300-1307. (Year: 2014).

Konya et al. Innate Lymphoid Cells in Graft-Versus-Host Disease. American Journal ofTransplantation 2015; 15: 2795-2801.

Pishdadian et al., "Type 2 Innate Lymphoid Cells: Friends or Foes-Role in Airway Allergic Inflammation and Asthma," Journal of Allergy, vol. 2012, Article ID 130937, 13 pages (2012).

Yasuda et al., "Contribution of IL-33-activated type II innate lymphoid cells to pulmonary eosinophilia in intestinal nematode-infected mice," PNAS, vol. 109, No. 9, pp. 3451-3456 (2012).

* cited by examiner

COMPOSITIONS AND METHODS FOR PREVENTING AND TREATING GRAFT VERSUS HOST DISEASE

CROSS-REFERENCE TO RELATED APPLICATIONS

This application is a divisional application of U.S. patent application Ser. No. 15/532,740, filed Jun. 2, 2017, herein incorporated by reference in its entirety, which is a national stage filing of International Application No. PCT/US2015/064001, filed Dec. 4, 2015, which claims priority under 35 U.S.C. § 119(e) to U.S. Provisional Patent Application Ser. No. 62/087,340, filed Dec. 4, 2014, herein incorporated by reference in its entirety.

GRANT STATEMENT

This invention was made with government support under Grant Nos. CA166794, CA072669, and HL115761 awarded by the National Institutes of Health. The government has certain rights in the invention.

TECHNICAL FIELD

The presently disclosed subject matter relates to compositions and methods for preventing and treating graft versus host disease (GvHD) and/or idiopathic pneumonia syndrome (IPS). The presently disclosed subject matter further relates to methods of making compositions for preventing and treating GvHD and/or IPS.

BACKGROUND

Graft versus host disease remains a major obstacle to the widespread utilization of allogeneic stem cell transplant (allo-SCT) and allogeneic bone marrow transplant (allo-BMT) for the treatment of high-risk or relapsed leukemia, lymphoid malignancies, myelodysplastic syndromes, myeloproliferative neoplasms, and bone marrow failure syndromes. While there has been progress in approaches to prevent acute GvHD (aGvHD), there has been little advancement in clinical approaches for the treatment of patients with aGvHD, which rely predominantly on systemic corticosteroids.

Unfortunately, corticosteroid therapy is associated with a substantial number of significant side-effects including infectious complications, bone disturbances and profound metabolic changes. The outcome for patients with steroid-refractory aGvHD is dismal with approximately 10% of these patients surviving one year after the diagnosis and little progress in improving this outcome over the past 20 years.

Similarly, idiopathic pneumonia syndrome (IPS) is a common pulmonary complication and remains a severe threat to survival after allo-SCT and allo-BMT. IPS often coincides with the onset of GvHD.

What are needed are therapies, methods of treatment and compositions for use in treating and/or preventing GvHD and IPS. Methods of making such therapeutics and effectively administering the same are also needed. Such advantages, and others disclosed herein, are provided by the instant disclosure.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

Provided herein are pharmaceutical compositions for treating graft versus host disease (GvHD) or idiopathic pneumonia syndrome (IPS). In some embodiments the compositions comprise a therapeutically effective amount of a cell preparation of IL-33 activated type 2 innate immune cells (ILC2), and a pharmaceutically acceptable carrier. In some embodiments the ILC2 cells have the following properties: test positive for expression of lymphoid marker CD90, test positive for expression of lymphoid marker ICOS, and test negative for expression of lymphohoid marker lin. In some embodiments the ILC2 cells test positive for expression of CD127, ST2, Sca-1, CD25, CD90, and ICOS, and test negative for expression of lin. In some embodiments the ILC2 cells are activated by cytokines IL-33, IL-25, IL-7 and/or combinations thereof. In some embodiments the ILC2 cells are derived from human cord blood cells. In some embodiments the pharmaceutical composition is substantially free of MPP2 cells.

Provided herein are in vitro methods for generating activated ILC2 cells, comprising in some embodiments collecting human cord blood from a subject, isolating c-Kit positive cells from the cord blood, and culturing the c-Kit positive cells in the presence of an IL-33 cytokine, whereby IL-33 activated ILC2 cells are generated. In some embodiments the ILC2 cells are activated by exposing the c-Kit positive cells in culture to cytokines IL-33, IL-25, IL-7 and/or combinations thereof. In some embodiments the in vitro methods further comprise analyzing the generated ILC2 cells by measuring expression of ST2 and CD127 in the ILC2 cells, whereby expression of ST2 and CD127 is indicative of the phenotype of ILC2 cells. In some embodiments the ILC2 cells are substantially free of MPP2 cells. In some embodiments the subject is a human patient or donor.

Provided herein are methods for treating graft versus host disease (GvHD) or idiopathic pneumonia syndrome (IPS) in a subject, comprising in some embodiments providing a subject in need of treatment for GvHD and/or IPS, and administering to the subject a therapeutically effective amount of a cell preparation of IL-33 activated ILC2 cells. In some embodiments the ILC2 cells have the following properties: test positive for expression of lymphoid marker CD90, test positive for expression of lymphoid marker ICOS, and test negative for expression of lymphohoid marker lin. In some embodiments the ILC2 cells test positive for expression of CD127, ST2, Sca-1, CD25, CD90, and ICOS, and test negative for expression of lin. In some embodiments the subject is a human subject receiving an allogeneic stem cell transplant (allo-SCT) or allogeneic bone marrow transplant (allo-BMT). In some embodiments the cell preparation of IL-33 activated ILC2 cells is administered to the subject within 1 to 30 days after receiving the allo-SCT or allo-BMT. In some embodiments the risk and/or severity of acute GVHD associated with allo-SCT or allo-BMT is reduced. In some embodiments the cell preparation of IL-33 activated ILC2 cells is administered as a co-infusion with the allo-SCT or allo-BMT. In some embodiments production of Th2 cytokines in the subject is increased, and/or production of Th1 and/or Th17 cytokines in the subject is decreased.

Provided herein are methods for preventing GvHD or IPS in a subject, comprising in some embodiments providing a subject receiving allo-SCT or allo-BMT, and administering to the subject a therapeutically effective amount of a cell preparation of IL-33 activated ILC2 cells. In some embodiments the cell preparation of IL-33 activated ILC2 cells is administered as a co-infusion with the allo-SCT or allo-BMT. In some embodiments the co-infusion of ILC2 cells with the allo-SCT or allo-BMT comprises infusion of the ILC2 cells at a time sufficiently proximate to the allo-SCT or allo-BMT to prevent or substantially prevent onset of GvHD or IPS. In some embodiments the ILC2 cells have the following properties: test positive for expression of lymphoid marker CD90; test positive for expression of lymphoid marker ICOS; and test negative for expression of lymphoid marker lin. In some embodiments the ILC2 cells test positive for expression of CD127, ST2, Sca-1, CD25, CD90, and ICOS, and test negative for expression of lin. In some embodiments production of Th2 cytokines in the subject is increased, and/or production of Th1 and/or Th17 cytokines in the subject is decreased.

Provided herein are methods of increasing production of Th2 cytokines in a subject, comprising: providing a subject in need of increased Th2 cytokine production, and administering to the subject a therapeutically effective amount of a cell preparation of IL-33 activated ILC2 cells. In some embodiments the subject comprises a human subject receiving allo-SCT or allo-BMT. In some embodiments production of Th1 and/or Th17 cytokines is decreased in the subject. In some embodiments the ILC2 cells have the following properties: test positive for expression of lymphoid marker CD90, test positive for expression of lymphoid marker ICOS, and test negative for expression of lymphoid marker lin. In some embodiments the ILC2 cells test positive for expression of CD127, ST2, Sca-1, CD25, CD90, and ICOS, and test negative for expression of lin.

Accordingly, it is an object of the presently disclosed subject matter to provide compositions and methods for preventing and treating GvHD and/or IPS. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

(FIG. 1A) ILC3 from the LP are radiation resistant. ILC3 from MLN (FIG. 1B) and LP CD4 T cells (FIG. 1C) are sensitive to radiation. ILC2 cells from the LP (FIG. 1D) and MLN (FIG. 1E) are sensitive to radiation. This represents two independent experiments, n=4 for each. T test using GraphPad™ software (GraphPad Software, Inc., La Jolla, Calif., United States of America), ** $p<0.05$.

(FIG. 3B) GvHD scores over time. (FIG. 3C) Percent survival in timed injection study. (FIG. 3D) GvHD scores of timed injection study. These represents 4 independent experiments, n=42. ** $p=0.01$, by Log-rank (Mantel-cox) test using GraphPad Prism™ 5 software (GraphPad Software, Inc., La Jolla, Calif., United States of America).

(FIG. 4A) ELISA quantification of GFP (Cell Biolabs: AKR-121; Cell Biolabs, Inc., San Diego, Calif., United States of America) in tissue homogenates on day 12 post BMT from Ctrl (open bars) and Treat 1:1 (grey bars) normalized to grams of tissue. Donor T cells from BMT (as described for FIG. 3A) were evaluated by flow cytometry 12 days after BMT, Ctrl (open bars) and Treatment (grey bars). (FIG. 4B) Percentage of donor T cells in the LP lymphocyte compartment (LPL). (FIG. 4C) The total number of CD4+ and CD8+ donor T cells in the LP. (FIG. 4D) Total number of IFN-γ producing donor Th1 and Tc1 and the number of donor IL-17A producing Th17 cells. (FIG. 4E) The percentage of donor Treg as determined by intranuclear staining of FoxP3. These represents 2 independent experiments, n=4 each. Student T test using GraphPad Prism™ software (GraphPad Software, Inc., La Jolla, Calif., United States of America), * $p<0.05$.

(FIG. 5A) ELISA quantification of ILC2 derived GFP in GvHD target organs. (FIG. 5B) Bar graph of average IL-13 and IL5 IC cytokine±SEM in donor ILC2 cells day 12 post BMT.

FIG. 8A is a plot showing the results of tolerogeneic dendritic cells from donor mice being enumerated using CD11c and CD103 as markers. FIG. 8B is a bar graph demonstrating that there is no increase in FoxP3-expressing T cells in the GI tract after bone marrow transplantation comparing mice receiving ILC2 cells (grey bar) with control treatment (open bar). FIG. 8C is a plot showing the results of haploidentical mice receiving lethal irradiation (BM only) and transplantation using wild type bone marrow cells supplemented with T cells with (Treatment) and without (Control) ILC2 cells.

DETAILED DESCRIPTION

Figure 1:
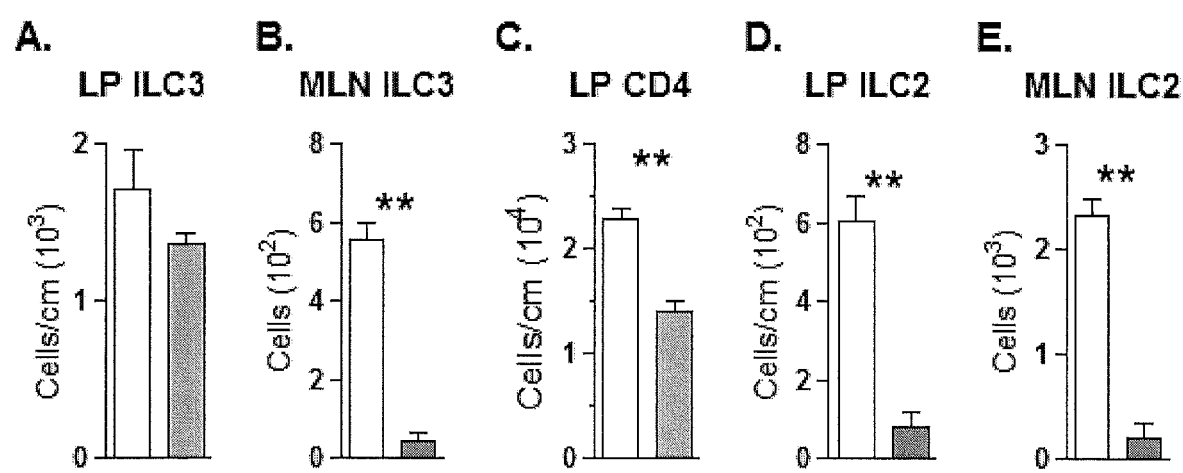
FIGS. 1A-1E are a series of bar graphs showing that ILC2 cells are radiation sensitive. Comparison of unconditioned cells (white bars) or 24 hours after receiving radiation (950 cGy) (grey bars) as analyzed by flow cytometry.

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

GvHD is mediated by donor T cells that recognize major and minor histocompatibility differences in the host. Evaluations using pre-clinical models and clinical studies have indicated that Th1 T cells and perhaps Th17 cells may be mediators of aGvHD. Moreover, in accordance with the presently disclosed subject matter, Th1 cells have been found to be involved in the pathogenesis of aGvHD involving the small bowel and colon.

The reason for the Th1 bias for GvHD involving the GI tract is not clear, although previous investigations have implicated the release of LPS and cytokine activation by host innate immune cells as a result of bacterial translocation after conditioning therapy. However, targeting this axis has not been substantially beneficial in the treatment of patients with steroid-refractory aGvHD.

New populations of innate cells that express similar cytokines and transcription factors compared to polarized T cells but lack germ-line encoded recombined receptors have been identified. An innate immune population of cells that generates Th2 cytokines is termed nuocytes or type 2 innate immune cells (ILC2). These cells generate substantial quantities of IL-5, and IL-13 with more modest expression of IL-4. These cells are involved in Th2 cell generation of IL-13 and the host response to specific parasitic infections. Human ILC2 cells can be found in the GI tract and lung and can be defined by their expression of CD161 and the chemoattractant, CRTH2 (Mjosberg et al., *Nat Immunol.* 2011; 12(11):1055-1062). Like murine ILCs, human ILC2 cells can be expanded in vitro and produce significant quantities of IL-5 and IL-13 in response to IL-7 and IL-33 (Yu et al., *Mucosal Immunol.* 2013).

T lymphocytes are characterized by the expression of the T cell receptor (TCR), which requires recombination of variable, diversity, joining and constant gene segments to produce a TCR capable of binding to peptide/MHC proteins. The generation of a T cell repertoire, with limited activity against self, occurs in the thymus. These naïve T cells recognize antigens presented by APCs, which leads to T cell activation, proliferation and differentiation leading to the generation of the adaptive immune response. As this process takes 7-10 days, mechanisms are needed to control pathogen growth during this time frame. Thus, the immune system has innate immune cells that can recognize pathogen-associated molecular patterns and/or damage-associated molecular patterns and initiate an immune response. This aspect of the immune response, which includes neutrophils, macrophages, dendritic cells and monocytes, is a critical part of the initial immune response.

New populations of innate immune cells have been discovered. Previously, NK cells that generate IFN-γ were discovered (Kiessling et al., 1976). Following this, other populations of innate cells were found. These cells were often located at mucosal sites such as the GI tract and lung, where they served a critical role as "first responders" to infectious pathogens. Three new groups of innate immune cells, ILC1 (generate IFN-γ similar to NK cells), ILC2 and ILC3 Is have been described. The first population of innate cells are lymphoid tissue inducer cells (LTi). These cells express the transcription factor RORγt and are involved in the generation of lymphoid tissue. Previous work has shown that fetal CD4+/CD3−/CD45+/IL-7Rα+ cells were important for the development of lymph nodes (LN) and Peyer's patches (PP). These cells, which are generated around day 12.5 during development, require the transcription factors Id2 and RORγt for their development. They express surface lymphotoxin (LT) α1β2, and were termed LTi cells. The absence of these cells or of the transcription factors necessary for their generation (Id2, RORγt), or proteins that mediate the interaction of LTα1β2 with LTβR on stromal cells leads to absence of LNs and PP.

It has also been determined that these LTi cells generated IL-17A and could be identified in mice after birth. A second group of cells that resemble LTi cells but are phenotypically distinct has been identified in mice after birth. These cells generate IL-22 but not IL-17A and are found at mucosal sites mostly in the small bowel and colon. These ILCs express NK cell-associated cytotoxicity receptors NKp44 in humans and NKp46 in mice. They are distinct from a population of ILCs that generates IL-17A and lacks the expression of NK receptors. These IL-22 generating ILCs critically require the expression of the transcription factor Ahr56.

Innate immune cells that generate IL-17 and/or IL-22 have been termed ILC3 cells. Following the description of these cells, a second entirely different population of innate lymphoid cells was characterized. Previous work had suggested that the cytokine, IL-25, affected a non-T, B or NK cell.

The instant disclosure pertains, at least in part, to ILC2 cells. Such cells have in some embodiments been found to express CD127, CD117, CD90 and CD25, respond to IL-25 and IL-33, and generate IL-5 and IL-13. Notably, a second but distinct population of cells that is IL-25-responsive is termed multipotent progenitor 2 (MPP2) cells and can generate multiple different myeloid cells. However, they appear to be different from true ILC2 cells as ILC2 cells do not give rise to myeloid progenitors.

As disclosed herein, cultures of ILC2 cells in the presence of IL-33 significantly increases their expression of IL-4, IL-5 and IL-13 and enhanced cell proliferation. Although ILC2 and MPP2 cells share common characteristics such as cytokine profile, lack of lineage markers and response to IL-25 and IL-33, their discordant expression of CD25, CD127 and CD90 and distinct multipotent potential suggest they are distinct populations. Type 2 ILC share similarities to Th2 and Treg cells expressing high levels of Th2 cytokines as well as regulatory receptors that are constitutively expressed on Tregs.

MPP2 cells can give rise to monocytes, macrophages, eosinophils and mast cells. These progeny are competent antigen presenting cells and the adoptive transfer of MPP2 cells promoted Th2 cytokine responses. IL-25 and IL-33 stimulation of ILC2 cells promoted M2 macrophage recruitment to visceral associated adipose tissue.

The generation of ILC2 cells requires the expression of the transcription factor Id268. Like Th2 cells, ILC2 cells express GATA-3, MAF and STATE. ILC2 cells appear to be important for the generation of T cells making IL-13. ILC2 cells are important to the immune response to helminths such as Nippostrongyloides brasiliensis, which require IL-25 for an adequate immune response. These data support a framework by which ILC2 cells are relevant in providing a suitable environment for the generation of Th2 T cells. These Th2 cells along with MPP2 cells can assist in the recruitment and activation of mast cells, basophils, eosinophils and B cells allowing for clearance of parasitic infections. However, overexuberant ILC2/Th2 responses may be detrimental as clinical syndromes such as asthma may be increased after ILC2/Th2 activation.

Thus, disclosed herein are therapeutic treatments and composition based on the role ILC2 cells play in the pathogenesis of GvHD and IPS, both of which are associated with allo-SCT and/or allo-BMT. Particularly, disclosed herein for the first time are therapeutic approaches and compositions based on the discovery that infusion of IL-33 activated ILC2 cells into patients with ongoing GvHD or IPS, or prior to onset of GvHD or IPS in a susceptible patient, substantially ameliorates the diseases and improves survival.

In some embodiments protocols and methods are provided for isolating, expanding, activating and identifying ILC2 cells, in some embodiments in vitro and/or ex vivo, to be used in therapeutic methods and compositions for GvHD and IPS. For example, and as detailed in the Examples below, in some embodiments IL-25 and/or IL-33 (in some embodiments with IL-7) can activate ILC2 cells inducing production of IL-4, IL-5 and IL-13. Activated ILC2 cells can in some embodiments be used in therapeutic methods and compositions to treat and/or prevent GvHD and IPS by, at least in some aspects, shifting the cytokine micro-environment away form Th1/Th17 to Th2.

Indeed, as described in detail in the Examples, it is demonstrated herein that ILC2 cells can in some embodiments be highly sensitive to radiation. Thus, without being bound by any particular theory or mechanism of action, it was surmised that the absence of recipient ILC2 cells in the colon and MLN, may lead to alterations in the microenvironment leading to Th1 polarization in the lower GI tract induced after allo-SCT or allo-BMT. Given ILC2 production of Th2 cytokines and the data indicating that shifting the cytokine micro-environment away form Th1/Th17 to Th2 reduces the severity of GVHD, it was hypothesized that co-transplantation of ILC2 cells could reduce aGvHD and IPS and increase survival after allo-SCT and allo-BMT.

As such, provided herein are pharmaceutical composition for treating GvHD and/or IPS. Such pharmaceutical compositions can comprise a therapeutically effective amount of a cell preparation of IL-33 activated ILC2 cells. The ILC2 cells in such a composition can be further characterized as testing positive for expression of lymphoid marker CD90 and/or ICOS, and/or testing negative for expression of lineage-specific lymphoid markers. Moreover, the ILC2 cells can in some embodiments test positive for expression of CD127, ST2, Sca-1, CD25, CD90, and/or ICOS, and/or test negative for expression of lineage markers. As described further in the Examples herein, in addition to being activated by IL-33, ILC2 cells can in some aspects be activated by cytokines IL-25 and/or IL-7, alone or in one or more combinations with IL-33. Moreover, the pharmaceutical compositions provided herein, including those comprising activated ILC2 cells, can be screened for and confirmed to be completely or substantially free of MPP2 cells.

The ILC2 cells that are grown and/or activated in vitro can be derived from any suitable source of ILC2 cells, including for example mammalian blood and/or blood products. In some embodiments, the ILC2 cells can be derived from human cord blood cells. Such human cord blood cells can be derived from a donor subject and/or from a patient's own cord blood.

The compositions provided herein, particularly those to be administered to a subject or patient, can in some embodiments comprise a pharmaceutically acceptable carrier.

In vitro, or otherwise ex vivo, methods are also provided herein for generating activated ILC2 cells, comprising expansion of ILC2 cells from a small number of cells, and activation of such cells to generate cytokines. Such methods can provide the activated ILC2 cells for use in the disclosed pharmaceutical compositions and related therapeutic methods and approaches. These in vitro methods can in some embodiments comprise collecting human cord blood (or other potential source of ILC2 cells from a subject such as peripheral blood stem cells and/or bone marrow), isolating c-Kit positive cells from the cord blood, and culturing the c-Kit positive cells in the presence of an IL-33 cytokine. By culturing the ILC2 cells in the presence of at least IL-33 cytokines the ILC2 cells can be activated. In some embodiments additional cytokines can exposed to the cultured ILC2 cells to further elicit an activated state, including for example IL-25 and IL-7. The IL-33, IL-25 and IL-7 cytokines can be exposed to the ILC2 cells in culture any combination thereof.

To confirm the presence of activated ILC2 cells in some embodiments a further step can comprise analyzing the generated ILC2 cells by measuring expression of ST2 and CD127 in the ILC2 cells. Expression of ST2 and CD127 is indicative of the phenotype of ILC2 cells. Such a confirmatory step can rule out the presence of MPP2 cells such that a composition can be characterized as being free or substantially free of MPP2 cells. Additionally, characterization of human ILC2 cells found that the cells expressed CRTH2 and CD161 characteristic surface markers for the expression of ILC2 cells.

In some embodiments treatment or therapeutic methods are provided herein, including treatments and therapeutic approaches for GvHD and/or IPS. For example, in some embodiments methods for treating GvHD or IPS in a subject are provided and can comprise providing a subject in need of treatment for GvHD and/or IPS, and administering to the subject a therapeutically effective amount of a cell preparation of IL-33 activated ILC2 cells. The cell preparation administered to a subject can comprise any cell preparation or composition as disclosed herein. For example, such ILC2 cells can have properties including, but not limited to expression of lymphoid markers CD90 and/or ICOS, and/or absence of lymphoid marker lin. In some embodiments, the ILCS cell composition administered to a subject can be characterized by testing positive for expression of CD127, ST2, Sca-1, CD25, CD90, and ICOS, and test negative for expression of lin.

The subjects to be treated with the disclosed methods of treatment can comprise any subject in need of therapy, including any subject suffering from or susceptible to GvHD, IPS or related condition. In some embodiments the subject can in some embodiments be a human subject receiving an allo-SCT or allo-BMT In some embodiments the cell preparation of IL-33 activated ILC2 cells can be administered to the subject within 1 to 30 days after receiving the allo-SCT or allo-BMT. In some embodiments, the cell preparation of IL-33 activated ILC2 cells can be administered to the subject within 1 to 365 days after the onset or diagnosis of lower GI tract inflammatory GvHD or IPS.

The methods of treatment disclosed herein can in some embodiments reduce the risk and/or severity of acute GvHD associated with allo-SCT or allo-BM by preventing the onset of these conditions or significantly improving the survivability and/or treatability of the conditions. In some embodiments, GvHD and/or IPS can be completely or substantially reversed or overcome. For example, in some embodiments the administration of activated ILC2 cells as provided herein can completely eliminate or substantially decrease the clinical score of lower GI tract GVHD commensurate with a marked decrease in diarrhea and/or abdominal pain or blood in the stool. In some embodiments treatment methods and therapeutic compositions as disclosed herein can also reverse the symptoms and signs of IPS, such as but not limited to shortness of breath, hypoxemia, or increased work of breathing.

In addition to treating GvHD and/or IPS, in some embodiments methods are provided for preventing GvHD or IPS in a subject. Such preventative methods can comprise providing a subject receiving allo-SCT or allo-BMT, and administering to the subject a therapeutically effective amount of a cell preparation of IL-33 activated ILC2 cells as a co-infusion to the allo-SCT or allo-BMT. By administering a cell preparation of IL-33 activated ILC2 cells as a co-infusion with the allo-SCT or allo-BMT, i.e. before, during or shortly after, the onset of GvHD and/or IPS can be prevented or at least substantially minimized. Thus, in some embodiments the disclosed treatments and related methods can comprise administering the cell preparations of IL-33 activated ILC2 cells as a co-infusion with the allo-SCT or allo-BMT. A co-infusion of ILC2 cells with the allo-SCT or allo-BMT can in some aspects comprise infusion of the ILC2 cells at a time sufficiently proximate to the allo-SCT or allo-BMT to prevent or substantially prevent onset of GvHD or IPS. In some embodiments a co-infusion of ILC2 cells with the allo-SCT or allo-BMT can comprise infusion of the ILC2 cells at a time sufficiently proximate to the allo-SCT or allo-BMT to treat and/or substantially reduce any GvHD or IPS symptoms that arise as a result of the allo-SCT or allo-BMT. For example, activated ILC2 cells can be infused at the time of transplantation (allo-SCT or allo-BMT) or after transplantation at the onset of symptoms suggestive of GVHD or IPS.

In some embodiments the methods comprising the administration of activated ILC2 cells can impact and cause a shift in the cytokine micro-environment in a subject away from Th1/Th17 to Th2. As discussed herein, subjects suffering from GvHD and/or IPS can have an overabundance of Th1/Th17 and reduced Th2. As such, shifting or rebalancing these cytokine levels by increasing the production of Th2 cytokines in the subject and/or decreasing production of Th1 and/or Th17 cytokines in the subject can ameliorate and/or treat one or more symptoms of GvHD and/or IPS. Accordingly, in some embodiments methods of increasing production of Th2 cytokines in a subject are provided, comprising providing a subject in need of increased Th2 cytokine production, and administering to the subject a therapeutically effective amount of a cell preparation of IL-33 activated ILC2 cells. In some embodiments a subject receiving such a treatment method can comprise a human subject receiving allo-SCT or allo-BMT.

Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

Subjects

The subject treated, screened, tested, or from which a sample is taken, is desirably a human subject, although it is to be understood that the principles of the disclosed subject matter indicate that the compositions and methods are effective with respect to invertebrate and to all vertebrate species, including mammals, which are intended to be included in the term "subject". Moreover, a mammal is understood to include any mammalian species in which screening is desirable, particularly agricultural and domestic mammalian species.

The disclosed methods and treatments are particularly useful in the testing, screening and/or treatment of warm-blooded vertebrates. Thus, the presently disclosed subject matter concerns mammals and birds.

More particularly, provided herein is the testing, screening and/or treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided herein is the treatment of livestock, including, but not limited to, domesticated swine (pigs and hogs), ruminants, horses, poultry, and the like.

In some embodiments, the subject to be used in accordance with the presently disclosed subject matter is a subject in need of treatment and/or diagnosis. In some embodiments, a subject can have or be believed to GvHD, IPS or related condition or phenotype, particularly those associated with allo-SCT and/or allo-BMT.

Formulations

The compositions of the presently disclosed subject matter comprise in some embodiments a composition that includes a pharmaceutically acceptable carrier. Any suitable pharmaceutical formulation can be used to prepare the adenovirus vectors for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, mannitol or another sugar, and phosphate-buffered saline (PBS).

It should be understood that in addition to the ingredients particularly mentioned above the formulations of this presently disclosed subject matter can include other agents conventional in the art having regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, the cytokines.

Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a composition of the presently disclosed subject matter include, but are not limited to intravenous. Alternatively, a composition can be deposited at a site in need of treatment in any other manner. The particular mode of administering a composition of the presently disclosed subject matter depends on various factors, including the distribution and abundance of cells to be treated, additional tissue- or cell-targeting features of the composition, and mechanisms for metabolism or removal of the composition from its site of administration.

Dosage

An effective dose of a composition of the presently disclosed subject matter is administered to a subject in need thereof. A "therapeutically effective amount" is an amount of the composition sufficient to produce a measurable response (e.g., a reduction in GvHD symptoms). In some embodiments, a therapeutically effective amount is an amount sufficient to reduction and/or ameliorate symptoms in a subject suffering from GvHD and/or IPS. In some embodiments, a therapeutically effective amount is an amount sufficient to improve the health, well-being, prognosis and/or survivability of a subject suffering from GvHD and/or IPS. In some embodiments, a therapeutically effective amount is an amount sufficient to reverse GvHD and/or IPS in a subject suffering from GvHD and/or IPS. In some embodiments, a therapeutically effective amount is an amount sufficient to prevent GvHD and/or IPS in a subject susceptible to GvHD and/or IPS, such as a subject receiving allo-BMT or allo-SCT. In some embodiments, a therapeutically effective amount is an amount sufficient to increase Th2 cytokine production in a subject suffering from GvHD and/or IPS, and/or decrease Th1 and/or Th17 cytokine production in a subject suffering from GvHD and/or IPS. In some embodiments a therapeutically effective amount can comprise an amount that allows for the tapering and discontinuation of other immunosuppressive drugs used to treat/prevent GVHD.

Actual dosage levels of active ingredients in the compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, and the condition and prior medical history of the subject being treated. However, it is within the skill of the art to start doses of the compositions at levels lower than required to achieve the desired therapeutic effect and to gradually increase the dosage until the desired effect is achieved.

After review of the disclosure of the presently disclosed subject matter presented herein, one of ordinary skill in the art can tailor the dosages to an individual patient, taking into account the particular formulation, method for administration to be used with the composition, and severity of the condition, e.g. GvHD and/or IPS. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods for Examples 1-6

Mice

C57BL/6J (H2b) (termed WT), BALB/c, and C57BL/6J× DBA/2 F1 (termed B6D2) were purchased from The Jackson Laboratory, Bar Harbor, Me., United States of America. The generation of enhanced GFP-expressing C57BL/6 mice has been described previously (Panoskaltsis-Mortari et al., Blood 2004; 103(9):3590-8). Donor and recipient mice were age-matched males between 8 and 16 weeks. All experiments were performed in accordance with protocols approved by the University of North Carolina Institutional Animal and Care Use Committee, Chapel Hill, N.C., United States of America.

Isolation and Expansion of ILC2 Cells 10 to 12 week old C57BL/6 mice are given 0.4 µg of recombinant mouse IL-17E/IL-25 (R&D systems) for 4 days. On day 5, the cells are isolated from the mesenteric lymph node (MLN) and by peritoneal lavage using 10% serum complete RPMI. ILC2 cells are isolated by negative selection with MAC column using biotinylated antibodies [(Anti-CD8α (53-6.7), anti-CD4 (RM 4.4), anti-CD3ε (145-2C11), anti-γδTCR (UC7-13DS), anti-TER119 (TER-119), anti-B220 (RA3-6B2), anti-CD11c (N418), anti-CD11b (M1/70), anti-NK1.1 (PK136), anti-CD19 (MB19-1), anti-Ly6G (1A8) and anti-CD49b (DX5)] and Streptavidin Microbeads (Miltenyi 130-048-101, Miltenyi Biotec, Cambridge, Mass., United States of America). Cells are cultured for six days in 10% RPMI-c with rIL-7 and rIL-33 (10 ng/ml) changing media every 2 days. On the sixth day the cell purity is determined by flow cytometry and purified if needed as described above. ILC2 activation was evaluated on day 6 by IC staining of IL-5 and IL-13 by flow cytometry.

Transplantation Models

Total T cells were isolated using Cedarlane T cell recovery column kit (Cedarlane Laboratories, Burlington, N.C., United States of America), followed by Ab depletion using PE-conjugated anti-mouse B220 and anti-mouse CD25 Abs (eBioscience, San Diego, Calif., United States of America) and magnetic bead selection using anti-PE beads (Miltenyi Biotec, Cambridge, Mass., United States of America). T cell depleted bone marrow was prepared as described by Coghill et al., Blood. 2010; 115(23):4914-22. The day prior to transplantation, recipient mice received either 950 cGy (B6D2) or 800 cGy (BALB/c) of total body irradiation. For B6 to B6D2 or B6 to BALB/c transplants, recipients were intravenously injected with either 4×10$^6$ T cells and 3×10$^6$ TCD BM cells, or 5×10$^5$ total T cells and 5×10$^6$ TCD BM cells, respectively. For ILC2 treatment groups, B6 or BALB/c mice also received 4×106 or 1×106 CD90+ ILC2 respectively. Mice were observed twice weekly for clinical GVHD signs and symptoms based on a previously established clinical scoring system (van Den Brink et al., Journal of Immunology. 2000; 164(1):469-80). ILC2 cells were given either at the time of bone marrow transplantation (supplemented with T cells) or 7 days after bone marrow transplantation. For tumor studies mice were given P815 or mBC-CML tumor cells at the time of bone marrow transplantation.

Evaluation of Radiation Sensitivity

B6D2 mice received 950 cGy of total body irradiation. 24 hours later cells were isolated and evaluated by flow cytometry. Total cell numbers were established from the absolute event count of live cells gated as Lineage negative, CD90+, ICOS+ or RORγt+ for ILC2 or ILC3 respectively or as CD4+ for T cells.

Stereomicroscopy

Organs from anesthetized animals were imaged with a Zeiss SteReo Lumar V12 microscope with GFP bandpass filter (Carl Zeiss Microlmaging, Inc., Thornwood, N.Y., United States of America) at room temperature. AxioVision (Carl Zeiss) software was used to determine GFP intensities. Control and treatment recipient organs were imaged using the identical magnification (mag) and exposure (exp) times on day +12: PP-exp 200 ms, mag 40×.

Organ GFP Quantification

Organs from recipient animals were homogenized and absolute GFP levels determine by ELISA (Cell Biolabs, Inc., San Diego, Calif., United States of America). Detailed experimental procedures were conducted as described by Coghill et al., Blood. 2010; 115(23):4914-22.

Cell Isolation from GvHD Target Organs

Spleen, liver, lung, and colon were excised and weighed. Lamina propria lymphocytes were isolated using the Miltenyi Lamina propria dissociation kit (130-097-410) as per the manufacturer's instructions (Miltenyi Biotec, Cambridge, Mass., United States of America). Livers and lungs were digested in a solution of 1 mg/ml collagenase A (Roche) and 75 U of DNase I (Sigma-Aldrich, St. Louis, Mo., United States of America) in RPMI 1640/5% newborn calf serum. Digested tissues were treated with ACK lysis buffer to remove RBCs and were passed through 100-µm pore size cell strainers. Leukocytes were collected at the interface of a 40%/80% Percoll (Sigma-Aldrich) in RPMI 1640/5% newborn calf serum. The pelleted cells were washed in PBS/2% FBS. Spleens were teased apart, treated with ACK lysis buffer, and washed in PBS/2% FBS.

Example 1

Type 2 Innate Lymphoid Cells are Radiation Sensitive

Initially, the effect of radiation therapy on the survival of ILCs was investigated. For this, B6D2 mice were given a lethal dose of radiation and cell survival was determined by flow cytometry. As shown by Hanash et al., ILC3 cells in the LP of the colon but not MLN are resistant to radiation (FIGS. 1A and 1B) (Hanash et al., Immunity. 2012; 37(2): 339-50). In addition, CD4+ T cells in the LP, spleen and MLN are sensitive to radiation showing significant reduction of total cells within 24 hrs (FIG. 1C). Interestingly, unlike ILC3 cells, ILC2 cells from the LP of the colon were highly sensitive to radiation. Additionally, similar to ILC3 cells, ILC2 cells in the MLN were exquisitely sensitive to the effects of irradiation. In fact, these cells were as radiation sensitive as conventional CD4+ T cells (FIGS. 1C and 1D). Thus, the absence of recipient ILC2 cells in the colon and MLN, may critically lead to alterations in the microenvironment leading to Th1 polarization in the lower GI tract induced after allo-SCT. Given ILC2 production of Th2 cytokines and the data indicating that shifting the cytokine micro-environment away form Th1/Th17 to Th2 reduces the severity of aGVHD, it was hypothesized that co-transplantation of ILC2 cells would reduce aGvHD and increase survival after allo-SCT.

Example 2

Isolation, Expansion and Activation of ILC2 Cells

Figure 2:
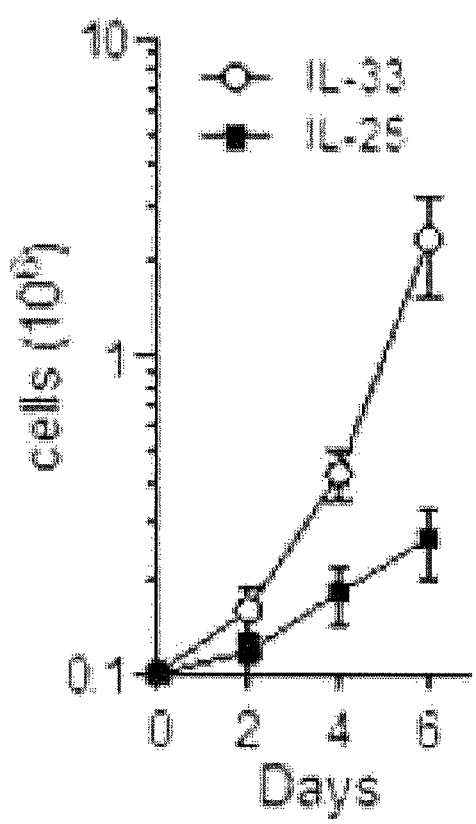
FIG. 2 is a line graph showing that IL-33 with IL-7 (open circles) treatment increases ILC2 proliferation in vitro compared to IL-25 with IL-7 (solid squares) (long/ml ea.), adjusted average cell number±SEM.

One obstacle to be addressed is the limited number of ILC2 cells in normal lymphoid tissue. To address this, a protocol was established for the isolation, expansion, and identification of ILC2 cells isolated from the mouse MLN and pertoneal cavity. ILC2 cells can be identified as CD90+, lin−, ICOS+ with additional expression of CD127, ST2, Sca-1, and CD25. Injection of IL-25 will elicit an increase in ILC2 cells in the MLN and peritoneal cavity and this method was adapted to expand ILC2 in vivo. After 4 days of IL-25 treatment intraperitoneal injection (i.p.) a significant increase in the number of ILC2 cells compared to control mice was found. However, this increase in ILC2 cells was insufficient to generate a significant population to use for in vivo transplantation. After isolation ILC2 cells were expanded in vitro with IL-33 and IL-7 treatment. With the use of IL-33 and IL-7 greater than 10 fold expansion of ILC2 cells in vitro after 6 days compared to IL-25 treated cultures (FIG. 2) was observed. There was a concern that an expansion of a second Lineage negative cell type in our culture had occurred. However, based their expression of additional ILC2 specific surface markers including CD127, ST2 and CD44, it was determined that the cells were bona fide ILC2. It was also determined that ILC2 cells lose expression of CD90 in culture. Further, IL-33 and IL-7 treatment also activates the ILC2 cells increasing the percentage of cultured cells that produced IL-4, IL-5 and IL-13 with no evidence of expansion of other ILC groups; IFN-γ in ILC1 cells; or IL-22 in ILC3 cells.

Thus, IL-25 and IL-33 activate ILC2 inducing production of IL-4, IL-5 and IL-13. IL-25 (0.4 ng/injection for 4 days) elicits increased ILC2 in the MLN of B6 mice. IL-33 with IL-7 treatment increases ILC2 proliferation in vitro compared to IL-25 with IL-7 (10 ng/ml each), adjusted average cell number±SEM. See FIG. 2. Lineage negative, IL-33 activated cells express ILC2 specific surface markers CD127, ST2 and CD44. IL-33 treatment activates ILC2 cells increasing cytokine production. Cells were isolated from MLN and by peritoneal lavage on day 5 of IL-25 injection and lineage depleted by bead separation (Miltenyi Biotec, Cambridge, Mass., United States of America).

To determine if the ILC2 cells that were generated ex vivo were significantly contaminated with MPP2 cells, the cells were analyzed for the expression of ST2 and CD127, which are not expressed by MPP2 cells. IT was shown that over 92% of the cells that were generated expressed ST2 and CD127, consistent with the phenotype of ILC2 cells.

Example 3

Co-Infusion of ILC2 Cells Reduces aGvHD and Increases Recipient Survival

Figure 3:
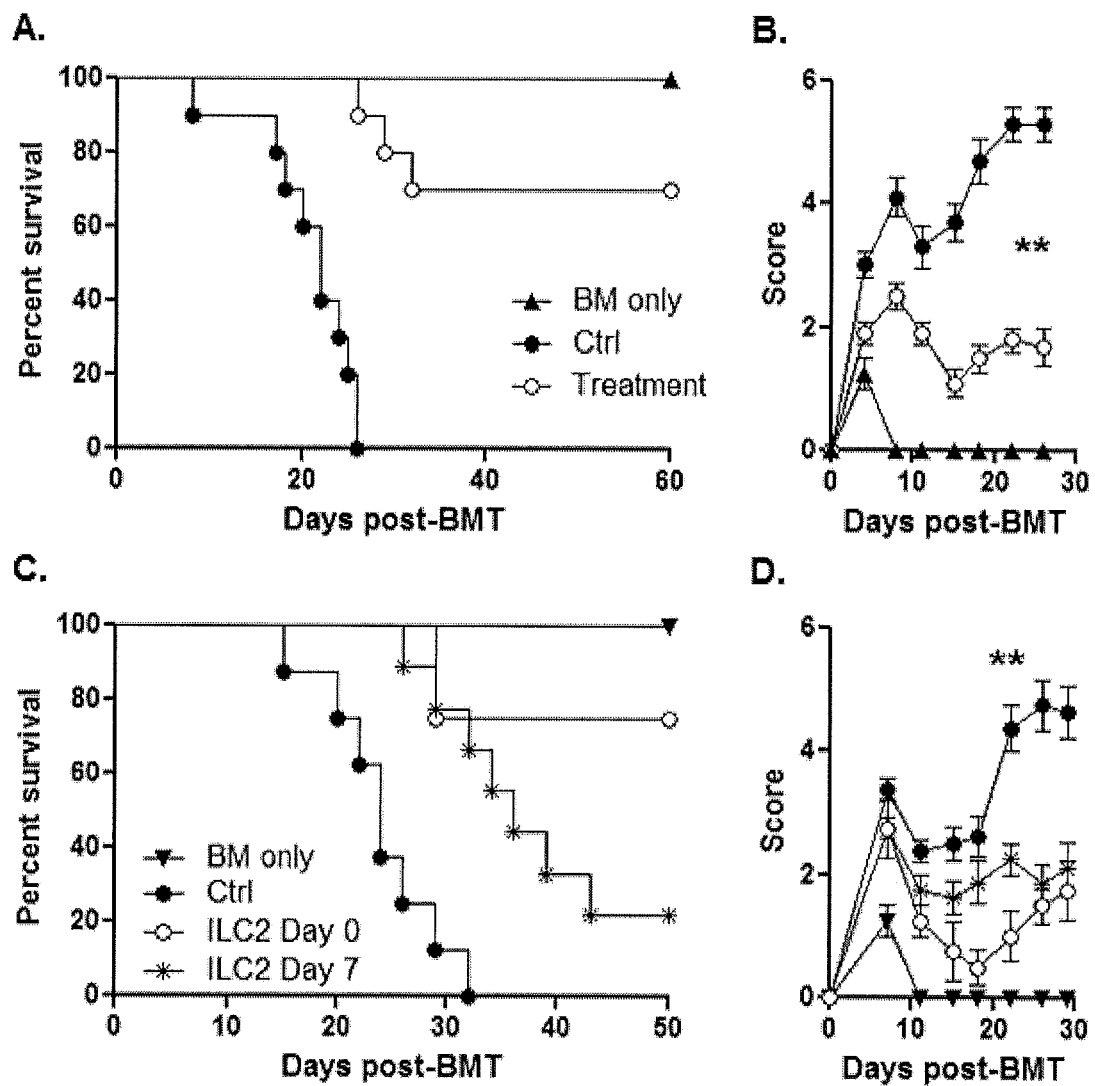
FIGS. 3A-3D are a series of plots showing that co-transplant of ILC2 cells reduces aGvHD. Lethally irradiated B6D2 mice (950 cGy) received 3.0×106 TCD BM (BM only), BM plus 4.0×106 total splenic T cells (Ctrl) or BM plus T cells with 4.0×106 IL-33 activated ILC2 cells (Treatment) in an ILC2 (Top row) or recipients received 4.0×106 IL-33 activated ILC2 cells at the time of allo-BMT or 7 days later (Bottom row) (FIG. 3A) Percent survival after allo-SCT.

Considering activated ILC2 cells expressed high levels of Th2 inducing cytokines, survival studies after allo-SCT co-infusing ILC2 cells were performed. For these experiments, splenic T cells were transplanted with (treatment) or without (ctrl) ILC2 cells. Interestingly, co-transplantation of one dose of ILC2 cells significantly improved survival in the B6 to B6D2 model of aGvHD with 70% of recipients surviving over 60 days (FIG. 3A). Recipients were monitored and scored for GVHD symptoms as previously described (van Den Brink et al., Journal of Immunology. 2000; 164(1):469-80, Fulton et al., Journal of immunology. 2012; 189(4):1765-72). As shown in FIG. 3B, there was a reduction in the clinical GvHD score in mice receiving ILC2 cells, beginning at day 10. In addition, a significant prolongation of survival was found in B6 into BALB/c transplants, a much more stringent MHC completely mis-matched model.

Survival studies were performed to determine if ILC2 cells can suppress established aGvHD by infusing ILC2 cells 7 days after transplant. Interestingly, with a single dose of ILC2 cells, survival was improved over untreated recipients (FIG. 3C). In addition, we observed a significant reduction in GvHD scores in those recipients of day 7 ILC2 injection beginning at day 20 (FIG. 3D). These findings have significant clinical implications as there is no cellular treatment for aGvHD after inflammation has begun.

Example 4

Figure 4:
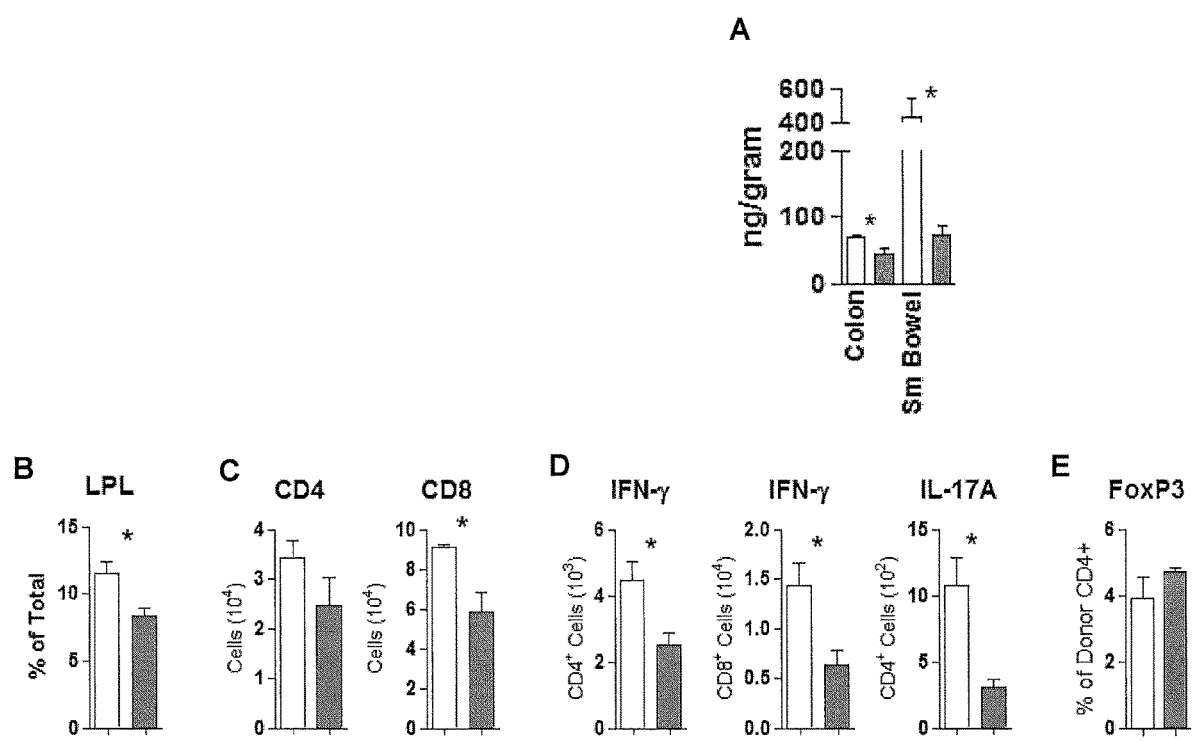
FIGS. 4A-4E are a series of bar graphs showing that co-transplant of ILC2 cells reduces donor T cells. Lethally irradiated B6D2 mice (950 cGy) received 3.0×106 TCD BM (BM only), BM plus 4.0×106 total splenic GFP+ T cells (Ctrl), BM plus GFP+ T cells with 4.0×106 ILC2 cells (Treat 1:1) or BM plus GFP+ T cells with 8.0×106 ILC2 cells (Treat 1:2). Donor T cells were evaluated in the GI tract 12 days after BMT.

Infused ILC2 Cells Reduce GI Tract T Cell Burden and Limit Th1 and Th17 Induction Donor T cell migration were evaluated using B6-GFP donor T cells and fluorescence stereomicroscopy and GFP ELISA. It was determined that co-infusion of ILC2 cells reduced donor T cells in Peyer's Patches (PP) in the colon and small bowel in a dose dependent manor as determined by GFP intensity. Using Zeiss SteREO microscopy with eGFP bandpass filter, GFP images were taken for each organ and GFP intensities were determined by software analysis. In addition, there is significantly less GFP in tissue homogenates. T cell infiltration into GvHD target organs was analyzed by flow cytometry and it was determined that those recipients of ILC2 cells had reduced lymphocytes in the LP of the colon (FIG. 4A). This finding correlated with reduced total CD4+ T cells and a significant reduction in CD8+ T cells (FIG. 4C). In addition, a significant reduction in the total number of CD4+ and CD8+ T cells that express IFN-γ was observed, as was reduced IL-17A producing CD4+ T cells (FIG. 4D). Interestingly, an increase in IL-4 producing donor T cells was not seen. The development of Treg cells was analyzed and only modest enhancement of FoxP3 expression was found (FIG. 4E). These data indicate that co-infusion of ILC2 reduces aGvHD by limiting the development of inflammatory Th1 and Th17 cells.

Example 5

Figure 5:
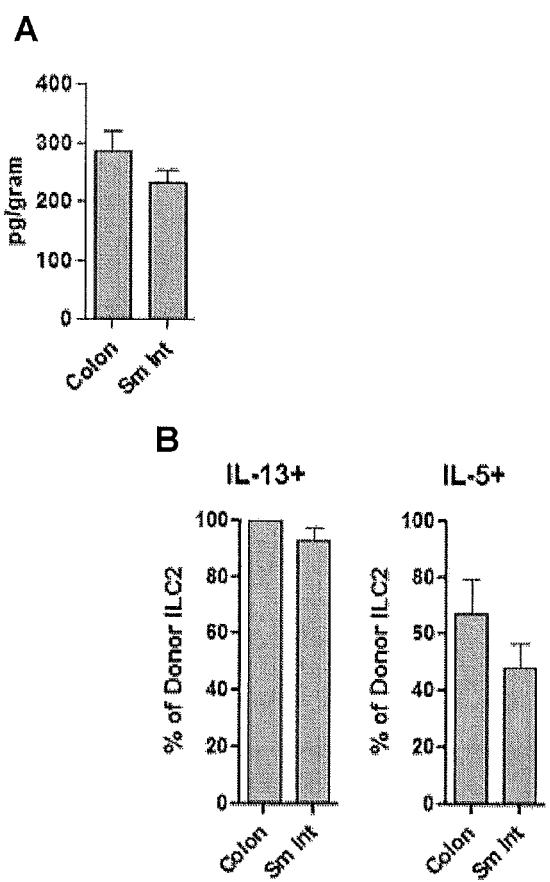
FIGS. 5A and 5B are a set of bar graphs showing that IL-33 activated ILC2 migrate to GvHD target organs and secrete Th2 cytokines. ILC2 cells were tracked using B6-GFP ILC2 donor mice for injection of IL-25 and in vitro expansion with IL-33 prior to co-infusion at BMT.

ILC2 Cells Migrate to Peyer's Patches in the GI Tract and Produce Th2 Inducing Cytokines LC2 migration to GvHD target organs was evaluated by infusing B6-GFP ILC2 cells. Particularly, ILC2 cells were tracked using B6-GFP ILC2 donor mice for injection of IL-25 and in vitro expansion with IL-33 prior to co-infusion at BMT. IVIS imaging of GFP expressing ILC2 cells in Peyer's patches 12 days after BMT in B6D2 mice was employed. While only limited GFP signal can be can be found in the lamina propria, large clusters of GFP-ILC2 cells were observed in the Peyer's patches on the intestine. Additionally, it was found that ILC2 cells migrate not only to the colon and small bowel but other GvHD target organs by measuring GFP in tissue by ELISA (FIG. 5A). Evaluating GFP positive ILC2 cells after transplant by flow cytometry confirms that the IL-33 activated cells that have been co-infused are innate lymphoid cells as determined by their expression of the lymphoid marker CD90 in the absence of other lineage defining markers including CD3, CD19, CD11b, CD11c, B220, Gr-1, NK1.1 or CD49b. It was also confirmed that these innate lymphoid cells are ILC2 by evaluating cytokine expression by intracellular staining IL-5 and IL-13 in ILC2 12 days after transplant. Greater than 90% of donor GFP positive IL-33 activated cells continue to express IL-13 in all target organs (FIG. 5B). Interestingly, IL-5 expression varies among GvHD target organs with more than 50% of ILC2 cells in the GI tract maintaining IL-5 expression. With the increased production of Th2 inducing cytokines in the GI tract we would expect an increase in Th2 expansion. As mentioned above there is not an increase in IL-4 producing T cells in mice that receive ILC2 cells.

Example 6

Human ILC2 Expansion

ILC2 cells were expanded from cord blood cells using the AhR antagonist SP1. Frozen umbilical cord blood cells were taken and stained with antibodies specific for CD34, c-Kit, CD90 and IL-7Rα. The presence of endogenous ILC2 cells in cord blood was analyzed and very few cells were found present. Thus, c-Kit+ cells were isolated from umbilical cord blood and put in the presence of the cytokines IL-33, IL-25 and IL-2 for cell expansion. There was robust expansion of ILC2 cells in the presence of the cytokines IL-2 and IL-33 and the presence of all three cytokines. This was a 10-fold increase over the 20 days in culture. When the cells were evaluated in culture at day 20, two different populations of cells were found—one that was c-Kithi and a second that was c-Kitlo. When the two different cell populations were analyzed, it was found that the c-Kithi population had decreased expression of IL-7Rα compared to the c-Kitlo population.

Example 7

Use of ILC2 Cells to Treat IPS

Figure 6:
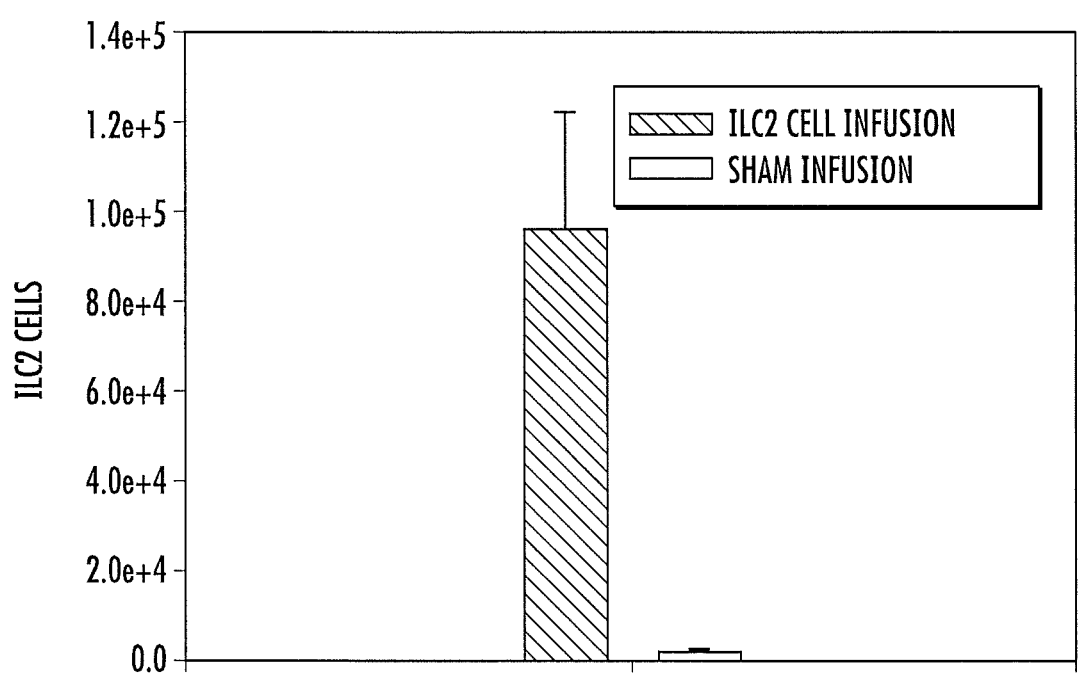
FIG. 6 is a bar graph showing enumeration of ILC2 cells after infusion from lung parenchyma. $1 \times 10^6$ ILC2 cells from eGFP+ mice were infused i.v. and 48 hours later evaluated from the lung parenchyma in B6D2 mice that had been lethally irradiated and received $3 \times 10^6$ B6 TCD bone marrow cells and 3.5×106 $B^6$ T cells. ILC2 cells were distinguished by the expression of GFP and in addition expression of ST2, CD127 and CD90 and absence of lineage markers. There was a strong statistically significant increase in ILC2 cells in the lung after i.v. infusion (hatched bar) that was not found in the sham treated animals (open bar) ($p<0.001$).

In addition to their ability to migrate into the LP of the GI tract, it was found that expanded ILC2 cells can migrate into the pulmonary parenchyma (FIG. 6). $1 \times 10^6$ ILC2 cells from eGFP+ mice were infused i.v. and 48 hours later evaluated from the lung parenchyma in B6D2 mice that had been lethally irradiated and received $3 \times 10^6$ B6 TCD bone marrow cells and $3.5 \times 10^6$ B6 T cells. ILC2 cells were distinguished by the expression of GFP and in addition expression of ST2, CD127 and CD90 and absence of lineage markers. There was a strong statistically significant increase in ILC2 cells in the lung after i.v. infusion that was not found in the sham treated animals ($p<0.001$).

Pulmonary GvHD and idiopathic pneumonia syndrome (IPS) are mediated predominantly by Th17 donor T cells. Yi et al., *Blood.* 2009; 114(14):3101-3112; Carlson et al., *Blood.* 2009; 113(6):1365-1374. Thus, ILC2 cells can be used to treat ongoing IPS by blocking the generation of Th17 cells.

Example 8

ILC2 Cells Function in the Absence of Th2 Polarization

B6D2 Recipient mice were lethally irradiated and administered donor T cells from B6 wild type or mice lacking the STAT6 gene which is critical for the generation of Th2 T cells. At the time of transplantation, one group of mice receiving STAT6 null T cells received ILC2 cells at a 1:1 ratio with T cells (T cell dose was $4 \times 10^6$ cells). The other group received PBS as a control. Overall survival and clinical score of GVHD were evaluated. N=8 mice/group. ILC2 cells are equally effective in preventing GVHD even when using T cells that cannot become Th2 cells.

Figure 7A:
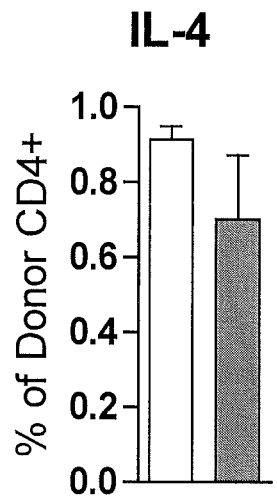
FIG. 7A is a bar graph indicating that there is no difference in the generation of T cells making IL-4 (Th2) after the infusion of ILC2 cells when comparing mice that received ILC2 cells (grey bar) and those receiving sham treatment (open bar) 12 days after bone marrow transplantation.
Figure 7B:
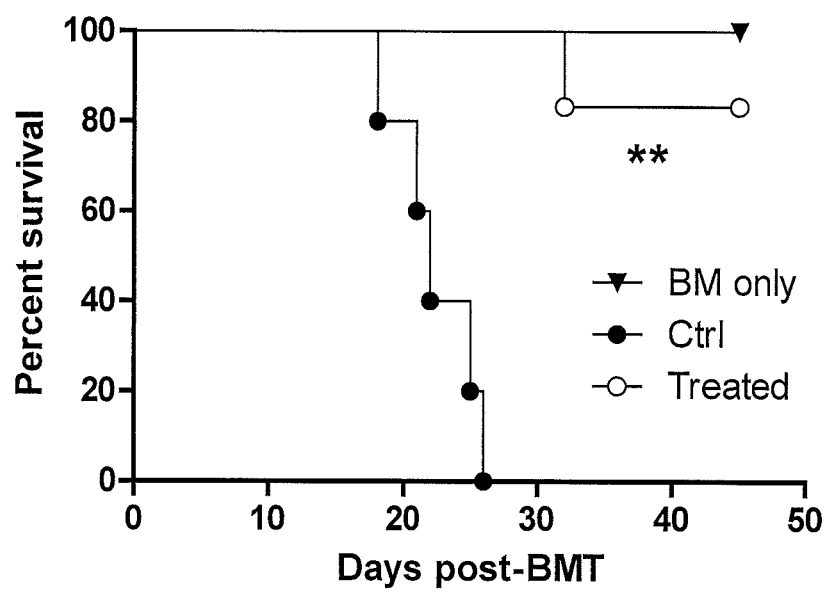
FIG. 7B illustrates the outcome of recipient mice receiving lethal irradiation (BM only) and infused with haploidentical wild type T cells with ILC2 cells (2:1) ratio (Control) or haploidentical STAT6 knockout T cells with ILC2 cells (2:1) ratio (Treated).
Figure 7C:
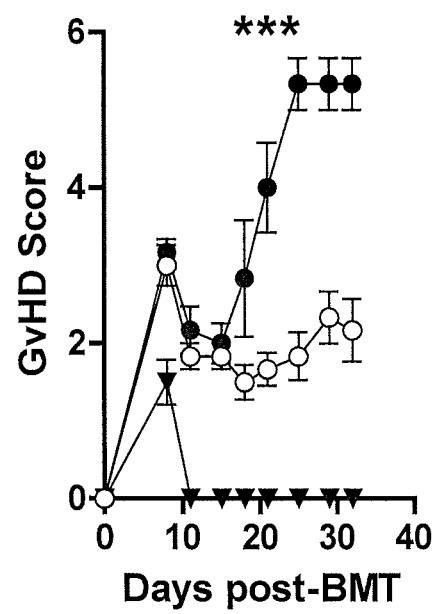
FIG. 7C is a plot showing the clinical scoring of recipient mice receiving lethal irradiation (triangle—BM only) and infused with either haploidentical WT T cells (closed circle—Control) or STAT6 knockout T cells plus ILC2 cells (open circle—Treated).
Figure 7D:
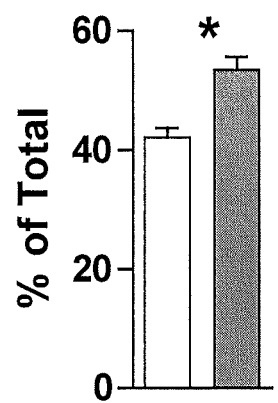
FIG. 7D is a bar graph showing an evaluation for FoxP3 expressing T cells in the GI tract 12 days after the administration of haploidentical WT T cells (open bar) or WT T cells supplemented 2:1 with ILC2 cells (closed bar).

FIG. 7A is a bar graph indicating that there is no difference in the generation of T cells making IL-4 (Th2) after the infusion of ILC2 cells when comparing mice that received ILC2 cells (grey bar) and those receiving sham treatment (open bar) 12 days after bone marrow transplantation. FIG. 7B illustrates the outcome of recipient mice receiving lethal irradiation (BM only) and infused with haploidentical wild type T cells with ILC2 cells (2:1) ratio (Control) or haploidentical STAT6 knockout T cells with ILC2 cells (2:1) ratio (Treated). STAT6 null T cells cannot generate Th2 cells. This figure demonstrates that the function of ILC2 cells to block GVHD is independent of the generation of Th2 cells. FIG. 7C is a plot showing the clinical scoring of recipient mice receiving lethal irradiation (triangle—BM only) and infused with either haploidentical WT T cells (closed circle-Control) or STAT6 knockout T cells plus ILC2 cells (open circle—Treated). Clinical scores are significantly improved in recipient mice given ILC2 cells with STATE knockout T cells compared to those given only WT T cells. FIG. 7D is a bar graph showing an evaluation for FoxP3 expressing T cells in the GI tract 12 days after the administration of haploidentical WT T cells (open bar) or WT T cells supplemented 2:1 with ILC2 cells (closed bar). This demonstrates that there is no quantitative increase in FoxP3-expressing regulatory T cells in the GI tract after ILC2 administration.

Example 9

ILC2 Cells Function by Enhancing GI Tract Myeloid Derived Suppressor Cells

Figure 8A:
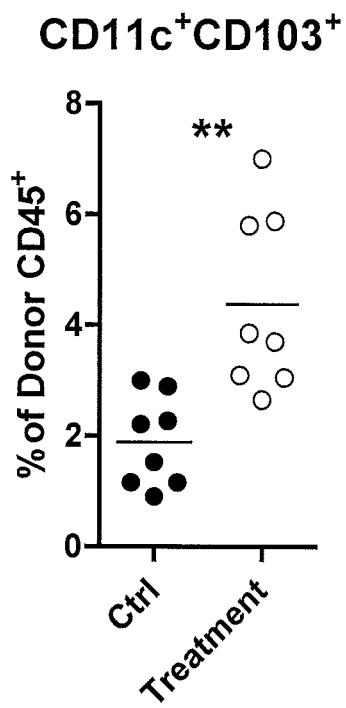
FIGS. 8A to 8C are a series of graphs and plots showing the results of an evaluating for the presence of donor antigen presenting cells in the GI tract in recipient mice after bone marrow transplant receiving ILC2 cells plus haploidentical T cells versus those receiving only haploidentical T cells.
Figure 8B:
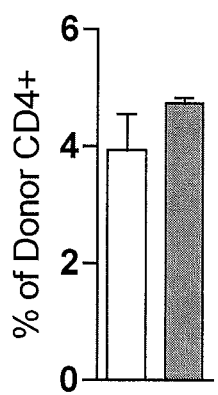
Figure 8C:
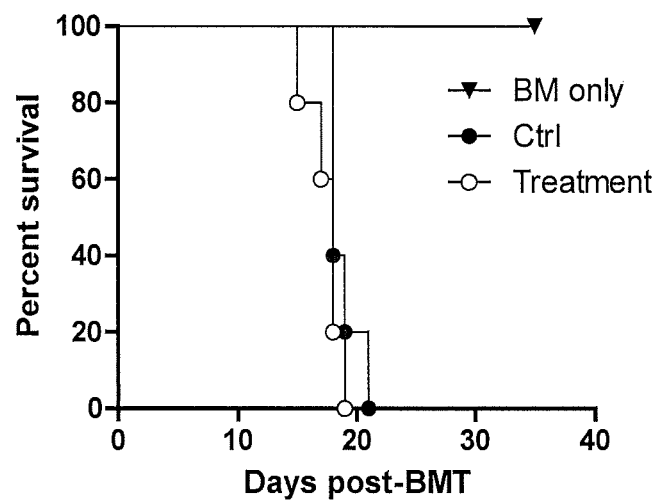

B6D2 recipient mice were lethally irradiated and administered $4 \times 10^6$ B6 T cells with/without a 1:2 ratio (ILC2 cells:T cells) of donor ILC2 cells. Following transplantation, mice were administered anti-GR-1 or anti-Ly6C mAb 2× per week for three weeks. As shown in FIGS. 8A to 8C, the activity of ILC2 cells to block GVHD was completely lost by depleting myeloid cells with these antibodies. In FIG. 8A tolerogeneic dendritic cells from the donor have been enumerated using CD11c and CD103 as markers. Mice receiving ILC2 cells have an increase in the number of tolerogenic DCs in the GI tract after transplantation. FIG. 8B again demonstrates that there is no increase in FoxP3-expressing T cells in the GI tract after bone marrow transplantation comparing mice receiving ILC2 cells (grey bar) with control treatment (open bar). In FIG. 8C haploidentical mice received lethal irradiation (BM only) and transplantation using wild type bone marrow cells supplemented with T cells with (Treatment) and without (Control) ILC2 cells. 2-3× per week after transplantation recipient mice received anti-Gr-1 monoclonal antibody by intraperitoneal injection (i.p.). Depletion of Gr-1-expressing cells completely eliminated the benefit of infusion of ILC2 cells to prevent GVHD. This indicates that ILC2 cell infusion is dependent on the presence of donor myeloid cells for its function.

Example 10

ILC2 Cell Infusion Diminishes GI Tract Permeability

Figure 9A:
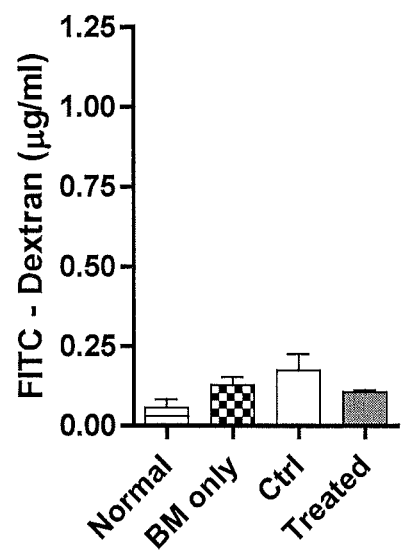
FIGS. 9A to 9E are a series of plots and graphs showing the results of the permeability of the GI tract from day 4 to 20 by administering FITC-dextran to mice after bone marrow transplantation which received either T cells with sham ILC2 infusion versus T cells with ILC2 infusion. Treatment groups in FIGS. 9A to 9C are as follows: Normal (lined bar); BM only (checkered bar); Control (open bar), Treated (grey bar). Treatment gropus in FIGS. 9D and 9E are as follows: BM only (triangle); Control (closed circle); Treatment (closed circle).
Figure 9B:
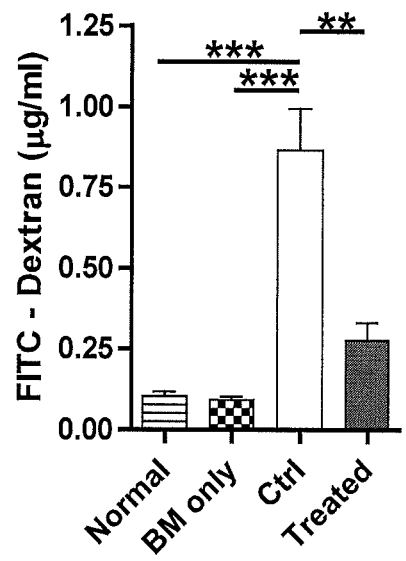
Figure 9C:
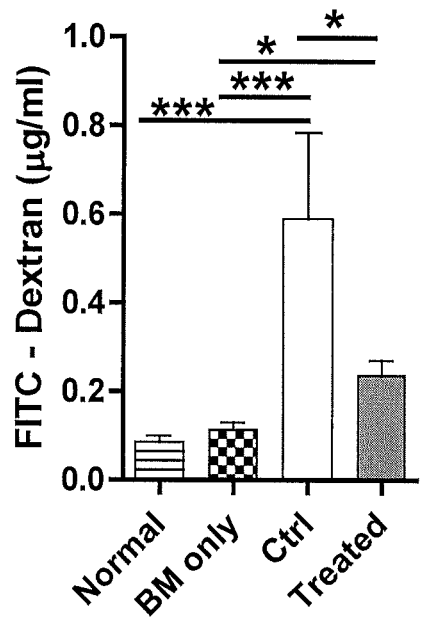
Figure 9D:
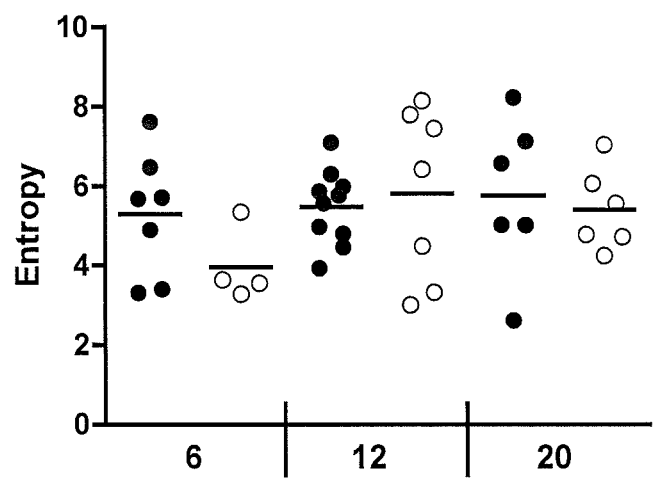
Figure 9E:
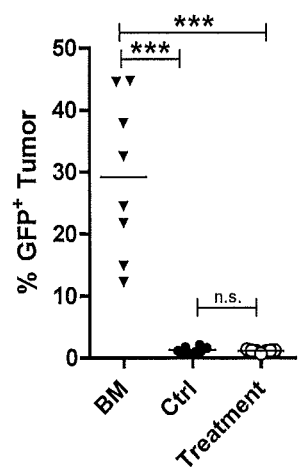

ILC2 cell infusion diminishes GI tract permeability and infectious complications that are associated with lower GI tract GVHD. As shown in FIG. 9A to 9E, the permeability of the GI tract we from day 4 to 20 was evaluated by administering FITC-dextran to mice after bone marrow transplantation which received either T cells with sham ILC2 infusion versus T cells with ILC2 infusion. There was a marked decrease in the leakage of FITC dextran from the GI tract in mice receiving T cells with ILC2 cells compared to T cells alone. This indicates that ILC2 cells decrease intestinal permeability and the translocation of GI tract flora after transplantation. Treatment groups in FIGS. 9A to 9C are as follows: Normal (lined bar); BM only (checkered bar); Control (open bar), Treated (grey bar). Treatment gropus in FIGS. 9D and 9E are as follows: BM only (triangle); Control (closed circle); Treatment (closed circle).

REFERENCES

1. Panoskaltsis-Mortari A, Price A, Hermanson J R, Taras E, Lees C, Serody J S, Blazar B R. In vivo imaging of graft-versus-host-disease in mice. Blood. 2004; 103(9): 3590-8. doi: 10.1182/blood-2003-08-2827. PubMed PMID: 14715632.
2. Coghill J M, Carlson M J, Panoskaltsis-Mortari A, West M L, Burgents J E, Blazar B R, Serody J S. Separation of graft-versus-host disease from graft-versus-leukemia responses by targeting C C-chemokine receptor 7 on donor T cells. Blood. 2010; 115(23):4914-22. doi: 10.1182/blood-2009-08-239848. PubMed PMID: 20185583; PubMed Central PMCID: PMC2890182.
3. van Den Brink M R, Moore E, Horndasch K J, Crawford J M, Hoffman J, Murphy G F, Burakoff S J. Fas-deficient lpr mice are more susceptible to graft-versus-host disease. Journal of immunology. 2000; 164(1):469-80. PubMed PMID: 10605044.
4. Hanash A M, Dudakov J A, Hua G, O'Connor M H, Young L F, Singer N V, West M L, Jenq R R, Holland A M, Kappel L W, Ghosh A, Tsai J J, Rao U K, Yim N L, Smith O M, Velardi E, Hawryluk E B, Murphy G F, Liu C, Fouser L A, Kolesnick R, Blazar B R, van den Brink M R. Interleukin-22 protects intestinal stem cells from immune-mediated tissue damage and regulates sensitivity to graft versus host disease. Immunity. 2012; 37(2):339-50. doi: 10.1016/j.immuni.2012.05.028. PubMed PMID: 22921121; PubMed Central PMCID: PMC3477611.
5. Neill D R, Wong S H, Bellosi A, Flynn R J, Daly M, Langford T K, Bucks C, Kane C M, Fallon P G, Pannell R, Jolin H E, McKenzie A N. Nuocytes represent a new innate effector leukocyte that mediates type-2 immunity. Nature. 2010; 464(7293):1367-70. doi: 10.1038/nature08900. PubMed PMID: 20200518; PubMed Central PMCID: PMC2862165.
6. Fulton L M, Carlson M J, Coghill J M, Ott L E, West M L, Panoskaltsis-Mortari A, Littman D R, Blazar B R, Serody J S. Attenuation of acute graft-versus-host disease in the absence of the transcription factor RORgammat.

Journal of immunology. 2012; 189(4):1765-72. doi: 10.4049/jimmunol.1200858. PubMed PMID: 22778391; PubMed Central PMCID: PMC3411855.

7. Yi T, Chen Y, Wang L, et al. Reciprocal differentiation and tissue-specific pathogenesis of Th1, Th2, and Th17 cells in graft-versus-host disease. *Blood.* 2009; 114(14):3101-3112.

8. Carlson M J, West M L, Coghill J M, Panoskaltsis-Mortari A, Blazar B R, Serody J S. In vitro-differentiated TH17 cells mediate lethal acute graft-versus-host disease with severe cutaneous and pulmonary pathologic manifestations. *Blood.* 2009; 113(6):1365-1374.

9. Mjosberg et al., *Nat Immunol.* 2011; 12(11):1055-1062.

10. Yu et al., *Mucosal Immunol.* 2013.

11. Kiessling et al., *J Exp Med.* 1976; 143(4):772-780.

All references listed herein including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for treating acute graft versus host disease (GvHD) in a subject, comprising:
   providing a subject in need of treatment for acute GvHD; and
   administering to the subject a therapeutically effective amount of a cell preparation of IL-33 activated ILC2 cells.

2. The method of claim 1, wherein the ILC2 cells have the following properties:
   positive for expression of lymphoid marker CD90;
   positive for expression of lymphoid marker ICOS; and
   negative for expression of lymphoid marker lin.

3. The method of claim 2, wherein the ILC2 cells are positive for expression of CD127, ST2, Sca-1, CD25, CD90, and ICOS, and negative for expression of lin.

4. The method of claim 1, wherein the subject is a human subject receiving an allogeneic stem cell transplant (allo-SCT) or allogeneic bone marrow transplant (allo-BMT).

5. The method of claim 1, wherein the cell preparation of IL-33 activated ILC2 cells is administered to the subject within 1 to 30 days after receiving the allo-SCT or allo-BMT.

6. The method of claim 1, wherein the risk and/or severity of acute GVHD associated with allo-SCT or allo-BMT is reduced.

7. The method of claim 1, wherein the cell preparation of IL-33 activated ILC2 cells is administered as a co-infusion with the allo-SCT or allo-BMT.

8. The method of claim 1, wherein production of Th2 cytokines in the subject is increased, and/or production of Th1 and/or Th17 cytokines in the subject is decreased.

* * * * *